US008133902B2

(12) United States Patent
Fenical et al.

(10) Patent No.: US 8,133,902 B2
(45) Date of Patent: Mar. 13, 2012

(54) AMMOSAMIDES AS ANTICANCER AGENTS (75) Inventors: William Fenical, Del Mar, CA (US); Paul Jensen, San Diego, CA (US); John MacMillan, Dallas, TX (US); Chambers C. Hughes, Del Mar, CA (US); James J. LaClair, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/666,269

(22) PCT Filed: Jun. 27, 2008

(86) PCT No.: PCT/US2008/068615
§ 371 (c)(1),
(2), (4) Date: Dec. 23, 2010

(87) PCT Pub. No.: WO2009/006319
PCT Pub. Date: Jan. 8, 2009

(65) Prior Publication Data
US 2011/0092534 A1     Apr. 21, 2011

Related U.S. Application Data (60) Provisional application No. 60/937,766, filed on Jun. 29, 2007.

(51) Int. Cl.
A61K 31/437 (2006.01)
C07D 471/06 (2006.01)
(52) U.S. Cl. ............... 514/296; 546/81; 546/84
(58) Field of Classification Search ............ None
See application file for complete search history.

(56) References Cited

FOREIGN PATENT DOCUMENTS
WO     WO 2007061694 A2     5/2007

OTHER PUBLICATIONS

Freshney, R. Ian, Liss, Alan R., Culture of Animal Cells, A Manual of Basic Technique, 1983, Wiley & Sons, Inc., New York, p. 4.*
Dermer, Gerald B., Another Anniversary for the War on Cancer, Mar. 12, 1994, Bio/Technology, 12, p. 320.*
Wrobel, Z. et al. Transformation of 2,2-dioxoisothiazolo[5,4,3-d,e]quinolones to pyrrolo[4,3,2-d,e]quinolin-2-(1H)-ones. Tetrahedron Letters. 2001, vol. 42, p. 5537.*
Alvarez et al., "Synthesis of Batzelline A, Batzelline B, Isobatzelline A, and Isobatzelline B," *Eur. J. Org. Chem.* (1999), 1173-1183, Wiley-VCH Verlag GmbH, Weinheim, Germany.
Balczewski and Joule, "Synthesis of Some Pyrrolo[4,3,2-de]guinolines," *J. Org. Chem.* (1994), 59(16):4571-4575, American Chemical Society.
Wrobel Zbigniew, "Transformation of 2,2-dioxoisothiazolo[5,4,3-d,e]quinolines to Pyrrolo[4,3,2-d,e]quinolin-2(1H)-ones," *Tetrahedron Letters* (2001), 42(32):5537-5539, Elsevier Science Ltd.

* cited by examiner

*Primary Examiner* — Rita Desai
*Assistant Examiner* — Ben S Michelson
(74) *Attorney, Agent, or Firm* — DLA Piper LLP (US)

(57)     ABSTRACT

A compound having the general the general structure I is provided: (Formula I), wherein Z is a substituent selected from a group consisting of S and O; X is a substituent selected from a group consisting of Cl, Br, I, OH and NH2; each of $R_1$ and $R_2$ is a substituent independently selected from a group consisting of H, a linear, cyclic or branched, substituted or unsubstituted $C_1$-$C_6$ alkyl, a substituted or unsubstituted aryl, and a substituted or unsubstituted heteroaryl; and each of Y and $Y_1$ is a substituent independently selected from a group consisting of H and C(O)—$C_6H_4$—Br.

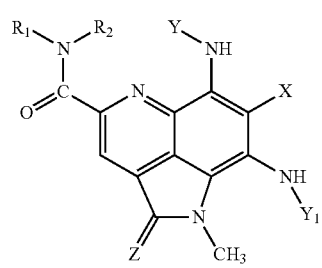

14 Claims, 5 Drawing Sheets

AMMOSAMIDES AS ANTICANCER AGENTS

CROSS REFERENCE TO RELATED APPLICATIONS

This application is a 35 USC §371 National Stage application of International Application No. PCT/US2008/068615 filed Jun. 27, 2008, now pending; which claims the benefit under 35 USC §119(e) to U.S. Application Ser. No. 60/937,766 filed Jun. 29, 2007, now abandoned. The disclosure of each of the prior applications is considered part of and is incorporated by reference in the disclosure of this application.

GRANT INFORMATION

This invention was made with government support under Grant No. CA44848 awarded by the National Institutes of Health. The government has certain rights in the invention.

BACKGROUND

1. Field of the Invention

The invention relates generally to anticancer agents derived from marine bacterial cultures. More specifically, it relates to anticancer compounds extracted from a marine-derived actinomycete.

2. Background Information

There exists a clear need for new drugs and pharmaceuticals to treat cancer and infectious diseases. Marine microorganisms are a valuable potential source of pre-clinical drug candidates. For example, marine natural products contain a diversity of molecules that target the cytoskeleton and cytoskeletal proteins including microfilaments, microtubules, and intermediate filaments play a role in the treatment of cancer, as their regulation by small molecules arrests progression through the cell cycle leading to a reduction in tumor growth.

For instance, jasplakinolide, a naturally occurring cyclic peptide, induces assembly and stabilization of actin microfilaments. Some polyketides, including halicondrin B and spongistatin, target microtubule stabilization, while phorboxazole B employs cytokeratin as a foundation to recruit critical cycle markers. One area of interest includes evaluation of deep-sea actinomycetes with an interest in identifying metabolites that target other components of the cytoskeleton. Accordingly, it is desirable to be able to isolate various compounds potentially having anticancer activity from a marine sediment. The present application provides such compounds.

SUMMARY

The present invention relates to new compounds having the general structure I:

wherein Z is a substituent selected from a group consisting of S and O; X is a substituent selected from a group consisting of Cl, Br, I, OH and $NH_2$; each of $R_1$ and $R_2$ is a substituent independently selected from a group consisting of H, a linear, cyclic or branched, substituted or unsubstituted $C_1$-$C_6$ alkyl, a substituted or unsubstituted aryl, and a substituted or unsubstituted heteroaryl; and each of Y and $Y_1$ is a substituent independently selected from a group consisting of H and $C(O)$—$C_6H_4$—Br, more specifically to compounds of the general structure I, wherein each of $R_1$ and $R_2$ is H.

More specifically, the present invention relates to new anticancer agents, i.e., ammosamide A and ammosamide B shown below as compounds IA and IB, respectively.

Compounds IA and IB shown above are obtained by cultivating an actinomycete strain CNR698-307 or CNR689-291, respectively, followed by chemical fractionalization to isolate the compounds.

Compounds IA and IB possess substantial anticancer activity, and are effective against the human colon cancer as well as a variety of other cancer types.

DETAILED DESCRIPTION

According to embodiments of the invention, compounds having the general structure I are provided:

wherein Z is a substituent selected from a group consisting of S and O; X is a substituent selected from a group consisting of Cl, Br, I, OH and $NH_2$; each of $R_1$ and $R_2$ is a substituent independently selected from a group consisting of H, a linear, cyclic or branched, substituted or unsubstituted $C_1$-$C_6$ alkyl, a substituted or unsubstituted aryl, and a substituted or unsubstituted heteroaryl; and each of Y and $Y_1$ is a substituent independently selected from a group consisting of H and C(O)—$C_6H_4$—Br, more specifically to compounds of the general structure I, wherein each of $R_1$ and $R_2$ is H.

In some embodiments of the invention, in compounds of the general structure I, each of $R_1$ and $R_2$ is H, and the compounds, therefore, have the structure IZ:

wherein Z is a substituent selected from a group consisting of S and O, X is a substituent selected from a group consisting of Cl, Br, I, OH and $NH_2$, and each of Y and $Y_1$ is a substituent independently selected from a group consisting of H and C(O)—$C_6H_4$—Br.

Some specific compounds of the invention described by the general structures I or IZ are compounds IA (ammosamide A) and IB (ammosamide B):

Compounds IA and IB are isolated in a pure form from a marine-derived actinomycete strain CNR698. More specifically, compound IA is obtained from the marine-derived actinomycete strain CNR698, and is the first natural product to contain a thio-β-lactam functionality. Compound IB is obtained from the marine-derived actinomycete strain CNR698. The actinomycete was obtained from a marine sediment. Briefly, the actinomycete, identified as a *Streptomyces* strain (CNR-698) was isolated from bottom sediments collected at a depth of 300 meters in the Bahamas Islands. Liquid shake flask fermentation in multiple 1 L scale, followed by solid phase extraction with Amberlite resin (XAD-7) and elution of the resin with acetone, gave a purple extract that showed significant activity against the HCT-116 colon carcinoma indicator cell line. Subsequent cytotoxicity-guided (HCT-116) fractionation by C18 flash chromatography and RP-HPLC led to the isolation of ammosamides A (compound IA) and B (compound IB) as dark blue and blue-purple, respectively (3 and 4 mg/L).

The compounds IA and IB and their analogues are intensely colored. Thiolactam compound IA appears blue in solution, though compound IB is blue-purple. The increased polarizability of the thiolactam (λmax 580 nm) produces a bathochromic shift in relation to compound IB (λmax 520 nm). N-acylation of compound IB results in an even larger bathochromic shift, affording green-blue products. N-methylation with MeI and potassium carbonate gives red-orange compounds (hypsochromic shift). Biosynthetically, compounds IA and IB are likely to originate from tryptophan biosynthesis. Ring closure along the N5-C5a bond, possibly through the pyrroloquinone, and a variety of aminations are required, analogous to the transformations observed in the microbial metabolite lymphostin.

More details concerning isolation, cultivation, and extraction leading to the isolation of compounds IA and IB, as well as the discussion of their structural and spectral characteristics are provided in the Examples portion of the instant application, below.

Other useful compounds of the present invention, described by the general structure I or IZ are compounds IC, ID and IE:

It has been determined that compounds of the general structure I or IZ, including compounds IA and IB, possess substantial anticancer activity and significant in vitro cytotoxicity against HCT-116 colon carcinoma, each with $IC_{50}$=320 nM. Accordingly, in some embodiments of the invention, compounds IA and IB are used for making pharmaceutical compositions comprising either or both of the two compounds and a pharmaceutically acceptable carrier. In addition, the pharmaceutical compositions can optionally comprise one or more additional anticancer agent(s).

These compounds IA and IB also demonstrated pronounced selectivity in a diversity of cancer cell lines with values ranging from ca. 20 nM to 1 μM, indicating a specific target mechanism of action. To explore the intracellular target of the ammosamides, compound IB was converted to a highly fluorescent molecule by conjugation with a dimethylaminocoumarin tag, as described below in detail in the "Examples" portion of the instant application. Treatment of HCT-116 colon carcinoma or HeLa cells with this fluorescent molecule produced immediate and irreversible labeling of a specific protein in the cellular cytosol, as also discussed below.

Such pharmaceutical compositions can be administered in therapeutically effective quantities to a subject in need thereof for inhibiting proliferation of mammalian cells, or for treating a mammalian cell proliferative disorder, such as cancer. The pharmaceutical compositions may be formulated to comprise any of the compounds of the present invention, or combinations thereof. The pharmaceutical compositions can further optionally include one or more additional therapeutic anticancer agents, including, but not limited to, such agents as (1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); (2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); (3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; (4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); (5) enzymes, including, L-asparaginase, and hydroxyurea, etc.; (6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); (7) platinum compounds (e.g., Cisplatin and Carboplatin, etc.); (8) monoclonal antibodies conjugated with anticancer drugs, toxins, and/or radionuclides, etc.; (9) biological response modifiers (e.g., interferons [e.g., IFN-.alpha., etc.] and interleukins [e.g., IL-2, etc.], etc.); (10) adoptive immunotherapy; (11) hematopoietic growth factors; (12) agents that induce tumor cell differentiation (e.g., all-trans-retinoic acid, etc.); (13) gene therapy agents; 14) antisense therapy agents; (15) tumor vaccines; (16) agents directed against tumor metastases (e.g., Batimistat, etc.), (17) inhibitors of angiogenesis, and (18) selective serotonin reuptake inhibitors (SSRI's).

In the broad sense, any cancer or tumor (e.g. hematologic and solid tumors) may be treated according to embodiments of the invention. Exemplary cancers that may be treated according to embodiments of the invention include, but are not limited to, head and neck cancer, brain cancer (e.g. glioblastoma multifoma) breast cancer, colorectal cancer, esophageal cancer, gastric cancer, hepatic cancer, bladder cancer, cervical cancer, endometrial cancer, lung cancer (non-small cell), ovarian cancer and other gynological cancers (e.g. tumors of the uterus and cervix), pancreatic cancer, prostate cancer, renal cancer, choriocarcinoma (lung cancer), skin cancer (e.g. melanoma, basal cell carcinoma), hairy cell leukemia, chronic lymphotic leukemia, acute lymphocytic leukemia (breast & bladder), acute myelogenous leukemia, meningeal leukemia, chronic myelogenous leukemia, and erythroleukemia.

The following examples are intended to further illustrate but not limit the scope of the invention.

Example 1

General Experimental Procedures

Spectroscopy $^1$H and $^{13}$C NMR spectra were recorded on a Varian INOVA-500 spectrometer with a 5 mm IDPFG probe or on a Varian Mercury 300 with an ASW probe. $^1$H NMR spectra were referenced to the residual DMSO-d$_6$ ($\delta$ 2.50 ppm) and the $^{13}$C chemical shifts were referenced to the DMSO-d$_6$ signal ($\delta$ 49.0 ppm). Low resolution MS were recorded on an Agilent HP 1100 Electrospray MS system in positive ion mode. HRMS were recorded in the Department of Chemistry, University of California, San Diego. Reversed phase HPLC purifications were performed on a Waters 600E system with Sedex ELSD detection. All solvents for HPLC were Fisher brand HPLC grade.

Fluorescence Microscopy

HeLa cells (ATCC CCL-2) were cultured in phenol red-free Dulbecco's modification of Eagle's medium (DMEM) with 4.5 g/L glucose, 4.5 g/L L-glutamine and 5% heat inactivated fetal calf serum (FCS) in glass-bottom dishes. The cells were synchronized using a double thymidine block. Phenol red, a common additive in DMEM, was not used during the culturing or experimentation. Fluorescent images were collected on a Nikon TE 2000 using irradiation with a mercury vapor lamp (Nikon), filtration through a dichroic filter set (FF409, Semrock) with an excitation at 377±50 nm, dichroic with >98% reflection at 344-404 nm and >98% transmission at 415-570 nm, and emission filter at 447±60 nm, focusing with an Oil Immersion Epiplan 60× objective (Zeiss), and image collection with an SPOT RT-KE color CCD Camera (Diagnostic Instruments Inc.).

Co-Immunoprecipitation from HCT-116 Cell Lysates

HCT-116 cells (ATCC CCL-2) were cultured in phenol red-free Dulbecco's modification of Eagle's medium (DMEM) with 4.5 g/L glucose, 4.5 g/L L-glutamine and 5% heat inactivated fetal calf serum (FCS). Probe 4 (as described below) was added at 5 µM in DMEM containing 0.5% DMSO and incubated for 12 h under 5% CO$_2$ atmosphere at 37° C. The cells were scraped from the plate, concentrated via centrifugation at 300 rpm at 4° C. for 5 min, washed three times with PBS pH 7.2 (5 mL), and lysed in PBS pH 7.2 (0.5 mL) containing protease inhibitor cocktail (Roche) by agitation through 30 gauge needle.

The crude lysate was centrifuged at 13,000 rpm for 5 min at 4° C. to isolate aggregates to remove insoluble matter and subjected to spin dialysis on a 9 kDa spin filter (iCON, Pierce Biotechnology) to concentrate the lysate to ~1 mg/mL in net protein. The latter step was not required, but provided higher protein concentration for subsequent co-IP analysis. Samples of the resulting lysate (300 µL) were precipitated with Affigel Hz containing 12.5 mg/mL of the XRI-TF35 mAb (50 µL). The resin was agitated for 12 h at 4° C. with the resin. The resin was then washed with 3×2 mL of ice cold DMEM.

Figure 4:
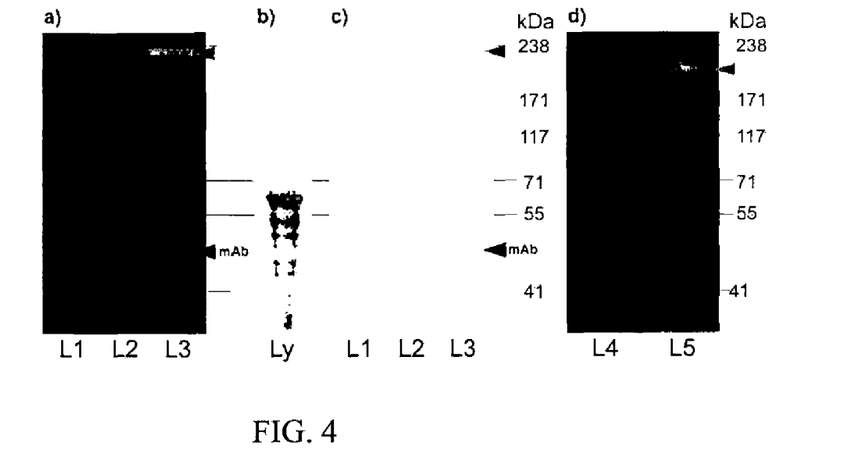
FIG. 4 is an illustration of the results of co-immunoprecipitation studies used in the evaluation of the mechanism of action of ammosamide B of the present invention.

The bound protein was then eluted from the resin by treatment with SDS page sample buffer containing 5-50 µM 7-dimethylamino-4-coumarin acetic acid (3, shown below) (lanes L2-L3, see FIG. 4a). In five repetitions, a band at ~220 kDa appeared after washing the resin with media containing compound 3 as a vehicle to release bound protein. Fluorescent SDS page gels were imaged with a CCD camera by excitation at 280 nm and emission through a 457±50 nm bandpass filter. The total protein content in each gel was determined by staining with GelCode Blue (Pierce).

Protein ID Analysis

Nano-LC/MS/MS analysis was conducted by contract services from the Center for Functional Genomics (CFG) at the University of Albany, State University of New York.

Validation of Myosin Binding

The binding of probe 4 to myosin was validated by examining the modification of commercial rabbit muscle myosin. An aliquot of rabbit muscle myosin at 100 µg/mL was treated with either 10 µM control 5 or 10 µM probe 4 in DMEM for 2 h at room temperature. Thereafter, each reaction was individually subjected to dialysis on a 9 kDa spin filter (iCON, Pierce Biotechnology) with 5 volumes of DMEM. Co-immunoprecipitation was conducted by treating a 200 µL sample of the dialyzed reaction mixture with Affigel Hz containing 12.5 mg/mL of the XRI-TF35 mAb (50 µL) for 4° C. After 12 hours, the resin was washed with 3×2 mL of ice cold DMEM. The washed resin was collected and treated with 50 µL of 50 µM 3 in SDS page loading buffer (Sigma-Aldrich) for 2 hours at room temperature. The solution was removed, boiled, and subjected to SDS page analysis on a 4% tris-glycine gel.

Mouse Tissue Histology

Figure 5:
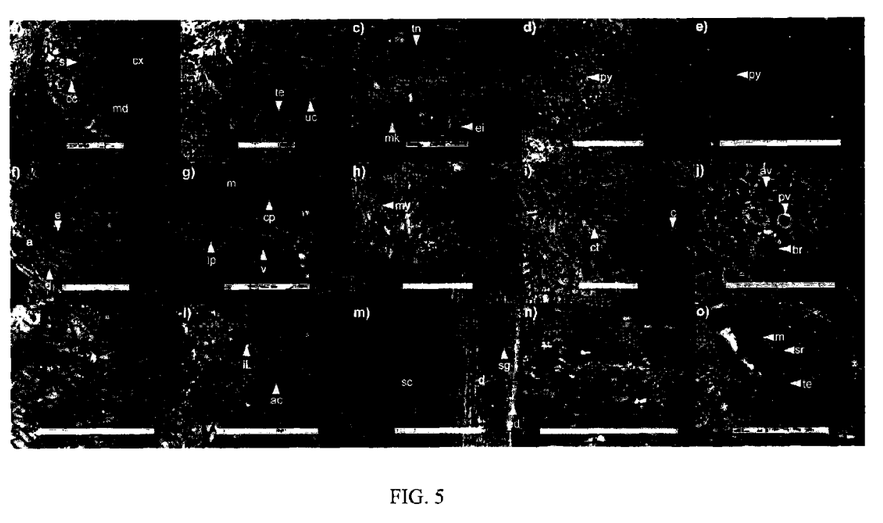
FIG. 5 is an illustration of the results of histological analysis used in the evaluation of activity of some compounds of the present invention.

A frozen mouse tissue microarray was prepared for treatment under the manufacturers protocols and then treated with 2 mL of 1 µM of probe 4 with mild rocking for 4 hours at room temperature. The plate was then washed with two volumes (2 mL) of 50% ethanol, 25% ethanol and then water, fixed and washed again with 3 volumes of water. Tissue microarrays treated under the same conditions with 2 mL of 1 µM control 5 were only weakly fluorescent under these conditions and provide a background that was less than 5-10% of the fluorescent intensity observed from probe 4 as shown in FIG. 5.

Example 2

Isolation of Strain CNR698, Cultivation and Extraction

*Streptomyces* sp. strain CNR698 was isolated on medium A1+C (10 g of starch, 4 g of peptone, 2 g of yeast extract, 1 g of calcium carbonate, 18 g of agar, 1 L of seawater) from a marine sediment collected at a depth of 300 m in the Bahamas in June, 2001. The strain was cultured in 20 1 L volumes of medium A1Bfe+C (4 g yeast extract, 2 g peptone, 10 g starch, 1 g CaCO$_3$, Fe$_2$(SO$_4$)$_3$, KBr, 1 L of seawater) while shaking at 230 rpm for 7 days. At the end of the fermentation period, 20 g/L XAD-7 adsorbent resin were added to each flask, and they were allowed to shake at a reduced speed for 2 additional hours. The resin was then collected by filtration through cheesecloth, washed with deionized water, and eluted twice with acetone to give a deep purple crude extract. Evaporation of the extraction solvent in vacuo left a wet residue that was taken up in methanol, providing approximately 80 mg of dry extract per 1 L of culture after removal of solvent.

Example 3

Isolation, Purification and Characterization of Ammosamide A (Compound IA) and B (Compound IB)

The acetone extracts from 20×1 L fermentations was initially separated using flash C$_{18}$ chromatography (10 cm×40 cm) eluting with solvent mixtures of 10:90 CH$_3$CN:H$_2$O, 20:80 CH$_3$CN:H$_2$O, 40:60 CH$_3$CN:H$_2$O, 60:40 CH$_3$CN:H$_2$O, 100:0 CH$_3$CN:H$_2$O. The 10:90 and 20:80 CH$_3$CN:H$_2$O fractions showed the most potent HCT-116 activity and by LC-MS contained two halogenated compounds (IA and IB)

with distinct UV absorbances. These two fractions had a distinct purple color and by RP TLC, IA appeared blue, while IB was pink. The two polar fractions were recombined and further purified by RP HPLC (Phenomenex Luna $C_{18}$, 5µ, 10×250 mm) with a gradient of 10:90 $CH_3CN:H_2O$ to 40:60 $CH_3CN:H_2O$ over 30 minutes to obtain pure ammosamide A (IA)(17-21 min) and ammosamide B (IB) (11.5-14 min). Typical yield from 1 L cultures of CNR698 were 3 mg/L and 4 mg/L for IA and IB respectively.

High-resolution (ESI) mass spectrometric analysis of ammosamide A (compound IA) indicated that it had the molecular formula $C_{12}H_{10}{}^{35}ClN_5OS$ [(M+H)$^+$ m/z=308.0303]. The molecular weight of ammosamide B (compound IB) was found to be approximately 16 Daltons lower [(M+H)$^+$ m/z=292.0604] indicative of the molecular formula $C_{12}H_{10}{}^{35}ClN_5O_2$. Other spectral data were indicative of a highly conjugated structure and were as follows.

Ammosamide A (IA Blue solid, UV (MeOH): 580, 430, 350, 290 nm. IR (neat): 1310, 1340, 1370, 1620, 1640, 3400, 3450 $cm^{-1}$. Ammosamide B (IB). Maroon solid, UV (MeOH): 600, 420, 360, 240 nm. IR (neat): 1312, 1343, 1605, 1660, 3410, 3455 $cm^{-1}$. See table 1 below for NMR data for both compounds IA and IB.

TABLE 1

NMR Spectral Data for Ammosamides A (IA) and B (IB)

| Position # | Ammosamide A (IA) | | | Ammosamide B (IB) | |
|---|---|---|---|---|---|
| | $^{13}C$ | $^1H$ | HMBC | $^{13}C$ | $^1H$ |
| 2 | 178.0 | — | | 160.2 | — |
| 3 | 117.3 | 8.48 (s) | C-2, C-8b, C-4, C=O | 115.3 | 8.36 (s) |
| 3a | 143.6 | — | | 140.6 | — |
| 4 | 145.4 | — | | 144.7 | — |
| 5a | 133.4 | | | 130.6 | |
| 6 | 137.6 | — | | 132.4 | — |
| 7 | 104.0 | | | 105.0 | |
| 8 | 135.6 | — | | 130.9 | — |
| 8a | 111.3 | — | | 106.3 | — |
| 8b | 120.5 | — | | 119.3 | — |
| 9 | 164.0 | 8.90 (s) | | 166.2 | 8.88 (s) |
| (CONH$_2$) | | 7.62 (s) | | | 7.61 (s) |
| N—Me | 34.1 | 4.03 (s) | C-2 | 28.6 | 3.60 (s) |
| NH$_2$ (C6) | — | 7.15 (bs) | C-7 | — | 6.18 (bs) |
| NH$_2$ (C8) | — | 6.82 (bs) | C-7, C-8a | — | 6.70 (bs) |

Spectra were acquired in DMSO-$d_6$ at 27° C. Exchangeable protons were determined by $D_2O$ exchange experiments. Positions of atoms indicated in Table 1 are as shown below:

Inspection of the $^1H$ NMR spectrum of compound IA in DMSO-$d_6$ revealed five singlets between δ 6.0 and 9.0 and one methyl singlet at δ 4.03, while the $^{13}C$ NMR spectra revealed the presence of 11 $sp^2$ hybridized carbons and a single $sp^{-3}$ hybridized carbon at δ 34.1 as can be seen from Table 1. The addition of $D_2O$ (20 µL) to the sample in DMSO-$d_6$ resulted in the immediate disappearance of $^1H$ NMR signals at δ 7.15 (br s, 2H), δ 6.82 (br s, 2H) and the slower disappearance of singlets at δ 8.90 (1H), and δ 7.62 (1H) (<10 min). The exchangeable protons at δ 7.15 and δ 6.82 were assigned as aromatic amines at C-6 and C-8 respectively (based on HMBC correlations), while the slow exchanging protons at δ 8.90 and δ 7.62 were assigned to a primary amide on the basis of COSY and HMBC correlations.

The only non-exchangeable hydrogen atoms were the methyl singlet at δ 4.03 and a one proton singlet at δ 8.48. The $^{13}C$ NMR spectrum of IA indicated the presence of two carbonyl groups ($δ_c$ 178.0 and 164.0) as well as two upfield $sp^2$ carbons (δ c 104.0 and 111.3). HMBC correlations between the downfield carbonyl ($δ_c$ 178.0) and the proton methyl singlet at δ 3.92 could define an N-methyl amide, though a carbon chemical shift so far downfield would not be expected. In addition to correlations from the aromatic δ 8.48 singlet, the only other HMBC correlations were from the exchangeable protons at δ 7.15 to C-7 ($δ_c$ 104.0) and from δ 6.82 to C-7 and C-8a ($δ_c$ 111.3).

Figure 6:
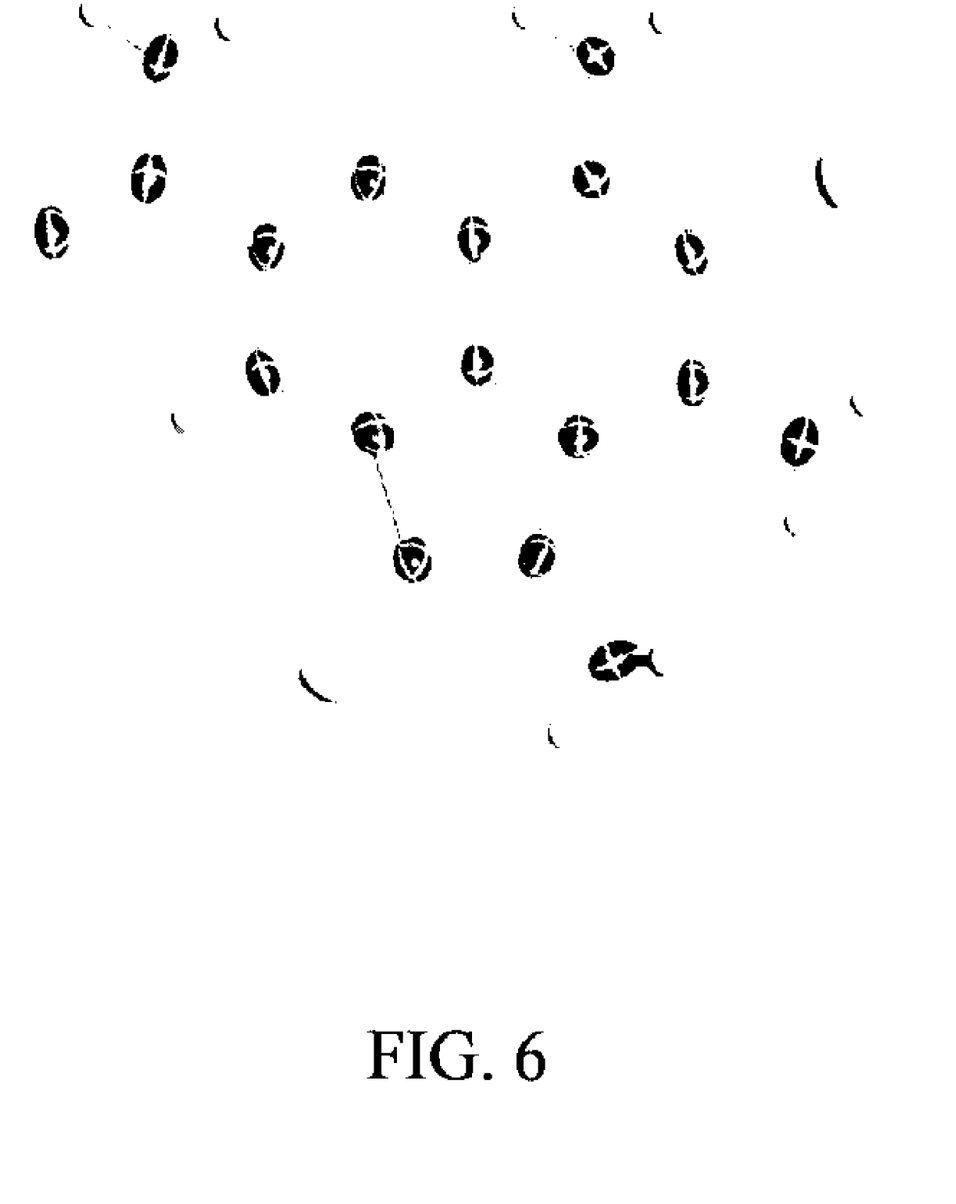
FIG. 6 is an illustration of an X-ray crystal structure of a compound of the present invention.

The overall spectral data for compound IA indicated a highly unsaturated aza-aromatic metabolite possessing three rings. To confirm the structure, an X-ray crystal structure was obtained (FIG. 6). Small crystals of compound IA were obtained by the slow diffusion of $H_2O$ into a saturated solution in DMSO. The X-ray assignment compound IA showed this compound to be the first example of a natural product possessing a thio-β-lactam ring. Once X-ray data became clear, the spectral data for compound IA could be partially assigned.

The structure assignment of compound IB followed from analysis of its spectral data and chemical interconversion. Comparison of the C-2 carbonyl chemical shifts in IA ($δ_C$ 178.0) and IB ($δ_C$ 160.2) revealed a difference of 17 ppm, consistent with the typical $^{13}C$ chemical shift difference between a carbonyl and a thio-carbonyl (~20 ppm). To chemically confirm the presence of the thiolactam functionality, Lawesson's reagent [2,4-bis(p-methoxyphenyl)-1,3-dithiadiphosphetane-2,4-disulfide] was used to convert lactam 2 into thiolactam 1 in 10% yield as shown on Scheme 1.

Scheme 1

As can be seen from Scheme 1, conversion of compound IB (2 on Scheme 1) to compound IA is accomplished using Lawesson's reagent, and the converse conversion occurs spontaneously and with hydrogen peroxide in aqueous methanol.

Example 4

Fermentation Studies for the Production of Br— and I— Analogs

The strain CNR698 was cultured in 10 1 L volumes of medium AlBfe+C (4 g yeast extract, 2 g peptone, 10 g starch, 1 g CaCO$_3$, Fe$_2$(SO$_4$)$_3$, KBr, and 1 L of artificial seawater replacing NaCl with NaBr and NaI respectively) while shaking at 230 rpm for 7 days. At the end of the fermentation period, 20 g/L XAD-7 adsorbent resin were added to each flask, and they were allowed to shake at a reduced speed for 2 additional hours. The resin was then collected by filtration through cheesecloth, washed with deionized water, and eluted twice with acetone to give a deep purple crude extract. Evaporation of the extraction solvent in vacuo left a wet residue that was taken up in methanol, providing approximately 50 mg of dry extract per 1 L of culture after removal of solvent.

Example 5

Isolation and Purification of Br-Ammosamide A (5), Br-Ammosamide B (6). I-Ammosamide A (7) and I-Ammosamide B (8)

Identical isolation procedures were used to obtain 5, 6, 7, 8, as were used for compounds IA and IB. Final RP C$_{18}$ HPLC purification with a gradient of 10:90 CH$_3$CN:H$_2$O to 40:60 CH$_3$CN:H$_2$O over 30 minutes gave 5 (19.4-21.0 min), 6 (11.6-13.0), 7 (19.8-20.3) and 8 (11.7-12.5). Purification of 7 and 8 was problematic due to the co-occurrence of IA and IB in the crude extract. Not all sources of chloride could be removed from the culture medium, giving rise to a 5:1 ratio of 1:7 and 2:8.

Bromo-ammosamide A (5). Blue solid, UV (MeOH): 600, 420, 360, 240 nm. ESI MS: obsd m/z 351.99 ([M+Na]$^+$, C$_{12}$H$_{11}$BrN$_4$OS requires 351.99. See $^1$H NMR data in table 2 below.

Bromo-ammosamide B (6). Maroon solid, UV (MeOH): 600, 420, 360, 240 nm. ESI MS: obsd m/z 336.01 ([M+Na]$^+$, C$_{12}$H$_{11}$BrN$_4$OS requires 336.01. See $^1$H NMR data in table 2 below.

Iodo-ammosamide A (7). Blue solid, UV (MeOH): 600, 420, 360, 240 nm. ESI MS: obsd m/z 398.96 ([M+Na]$^+$, C$_{12}$H$_{11}$IN$_4$OS requires 398.97. See $^1$H NMR data in table 2 below.

Iodo-ammosamide A (8). Maroon solid, UV (MeOH): 600, 420, 360, 240 nm. ESI MS: obsd m/z 383.00 ([M+Na]$^+$, C$_{12}$H$_{11}$IN$_4$OS requires 382.99. $^1$H NMR data are shown in table 2 below.

TABLE 2

$^1$H NMR Spectral Data of Ammosamides A and B Derivatives in DMSO-d$_6$ (500 MHz)

| Position | 5 $^1$H | 6 $^1$H | 7 $^1$H | 8 $^1$H |
|---|---|---|---|---|
| 2 | — | — | — | — |
| 3 | 8.45 (S) | 8.44 (s) | 8.28 (s) | 8.21 (s) |
| 3a | — | — | — | — |
| 4 | — | — | — | — |
| 5a | — | — | — | — |
| 6 | — | — | — | — |
| 7 | — | — | — | — |
| 8 | — | — | — | — |
| 8a | — | — | — | — |
| 8b | — | — | — | — |
| 9 (CONH$_2$) | 8.92 (s) | 8.90 (s) | 8.85 (s) | 8.65 (s) |
|  | 7.64 (s) | 7.60 (s) | 7.56 (s) | 7.45 (s) |
| N—Me | 4.06 (s) | 3.97 (s) | 3.58 (s) | 3.57 (s) |
| NH$_2$ (C6) | 6.96 (bs) | 6.89 (bs) | 6.05 (bs) | 6.01 (bs) |
| NH$_2$(C8) | 6.53 (bs) | 6.31 (bs) | 6.52 (bs) | 6.54 (bs) |

Example 6

Preparation of Ammosamide A mono-4-bromobenzoate (Compound IC) and Ammosamide A di-4-bromobenzoate (Compound ID)

Ammosamide A (IA) (1.5 mg) was dissolved in anhydrous pyridine (1.0 mL) followed by the addition of 4-bromobenzoyl chloride (30 μL) and heated to 50° C. for 14 hours to give a 2:1:1 mixture of mono- and di-4-bromobenzoate derivatives and starting material. The reaction was quenched by the addition of H$_2$O (100 μL). The mixture was extracted with EtOAc (250 μL×3) and concentrated in vacuo to give a orange solid. Purification by RP C$_{18}$ (Phenomenex Luna, 5μ, 250×10 mm) using isocratic conditions (52:48 CH$_3$CN: H$_2$O) gave pure ammosamide A di-4-bromobenzoate (ID) as a orange solid (0.7 mg) and ammosamide A mono-4-bromobenzoate (IC) as a orange solid (0.3 mg). The structures of both benzoate derivatives are shown below.

ammosamide A di-4-bromobenzoate ammosamide A mono-4-bromobenzoate

Ammosamide A mono-4-bromobenzoate (IC). Orange solid, UV (MeOH) 520, 418, 330, 245 nm. ESI MS: obsd m/z 489.90 ([M+Na]$^+$, C$_{12}$H$_{11}$IN$_4$OS requires 489.97. $^1$H NMR (DMSO-d6) δ 10.59 (s, NH-amide), 8.52 (s, H-3), 8.16 (d, 4.6 Hz, H-2', H-6'), 7.91 (s, primary amide), 7.62 (s, primary amide), 7.59 (d, 4.6 Hz, H-3', H-5'), 7.02 (s, NH$_2$), 4.05 (s, N-Me).

Ammosamide A di-4-bromobenzoate (ID). Red solid, UV (MeOH) 500, 412, 325, 240 nm. ESI MS: obsd m/z 670.92 ([M+Na]$^+$, C$_{12}$H$_{11}$IN$_4$OS requires 670.91. $^1$H NMR (DMSO-d6) δ 10.59 (s, NH-amide), 10.31 (s, NH-amide), 8.47 (s, H-3), 8.11 (d, 4.6 Hz), 8.01 (d, 4.7 Hz), 7.99 (s, primary amide), 7.57 (s, primary amide), 7.53 (d, 4.7), 7.46 (d, 4.6 Hz) 3.95 (s, N-Me).

Example 7

Preparation of Ammosamide B mono-4-bromobenzoate (Compound IE)

The same procedure was followed for the preparation of compound IE, as the one described above. The product was exclusively the mono derivative even after prolonged exposure to 4-bromobenzoyl chloride at elevated temperatures. The structure of the compound is shown below.

ammosamide B mono-4-bromobenzoate

Ammosamide B mono-4-bromobenzoate (IE). Orange solid, UV (MeOH) 505, 410, 320, 245 nm. ESI MS: obsd m/z 474.00 ([M+Na]$^+$, $C_{12}H_{11}IN_4OS$ requires 473.99. $^1$H NMR (DMSO-d6) δ 10.60 (s, NH-amide), 8.41 (s, H-3), 8.02 (d, 4.6 Hz, H-2', H-6'), 7.99 (s, primary amide), 7.79 (s, primary amide), 7.81 (d, 4.6 Hz, H-3', H-5'), 6.38 (s, NH$_2$), 3.68 (s, N-Me).

Example 8

Preparing Probes Comprising Ammosamide

Figure 1:
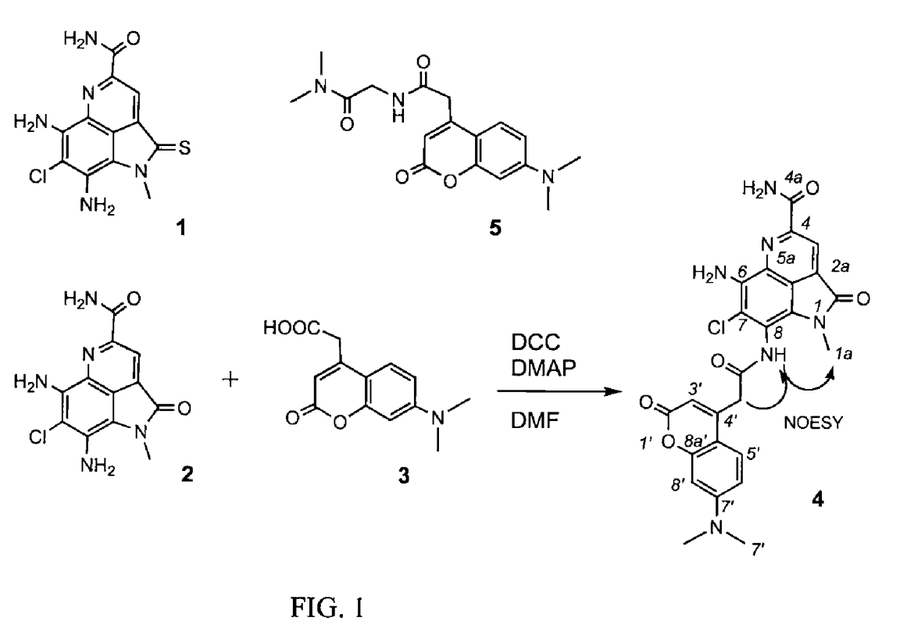
FIG. 1 is an illustration including the structure of a probe made using a compound of the present invention.

A probe was prepared as illustrated by FIG. 1. Samples of probe 4 were prepared by coupling 7-dimethylaminocoumarin-4-acetic acid (3) to ammosamide B (2, IB) with DCC/DMAP in DMF at room temperature. The coumarin location was derived by NOE correlations observed as shown in 4. FIG. 1 also illustrates the structures of ammosamide (A) (1) and control dye (5). $^1$H NMR data characterizing the probe 4 are shown in table 3 below.

TABLE 3

| $^1$H NMR Spectral Data of Ammosamide Probe 4 in DMSO-d$_6$ (500 MHz) | | | |
|---|---|---|---|
| Position as depicted in FIG. 1 | $δ_C$ | $δ_H$, mult. (J, Hz) | HMBC |
| 2 | 164.9 | | |
| 2a | | | |
| 3 | 114.9 | 8.42, s | 2, 5b |
| 4 | 150.5 | | |
| 4a | | | |
| 5a | | | |
| 5b | 119.0 | | |
| 6 | | | |
| 7 | 112.5 | | |
| 8 | 133.6 | | |
| 8a | 123.4 | | |
| 1-NMe | 27.0 | 3.28, s | 2, 8a |
| 4a-NH$_2$ | | 9.03, br s | 4 |
| | | 7.87, br s | |
| 6-NH$_2$ | | 6.70, br s | 6, 7 |
| 8-NH | | 10.37, brs | 10 |
| 2' | 160.5 | | |
| 3' | 109.7 | 6.20, s | 2, 4a, 9 |
| 4' | 150.1 | | |
| 4a' | 108.2 | | |
| 5' | 126.1 | 7.71, d (9.0) | 4, 7, 8a |
| 6' | 108.6 | 6.77, dd (9.0, 2.4) | 4a, 8 |
| 7' | 152.9 | | |
| 8' | 97.1 | 6.58, d (2.4) | 6, 8a |
| 8a' | 155.3 | | |
| 9' | 38.3 | 4.00, s | 3, 4, 4a, 10 |
| 10' | 168.6 | | |
| 7'-NMe$_2$ | 39.5 | 3.04, s | 7,7-NMe$_2$ |

Example 9

Evaluation of the Uptake and Localization of Ammosamides A (IA) and B (IB)

Evaluation of the uptake and localization of the above described ammosamides A (IA) and B (IB) was conducted using the method of fluorescent derivatization, because while bright blue in color, ammosamides A and B lack sufficient fluorescence to be evaluated at physiologically relevant levels.

Using an immunoaffinity fluorescent (IAF) system, 7-dimethylamino-coumarin-4-acetamide was elected as the tag, as it lacked toxicity, offered synthetic flexibility, and served both as fluorescent label and as an epitope to monoclonal antibody (mAb). Ammosamide B (2 IB) was coupled with tag 3 to provide crude probe 4 (FIG. 1), which was then purified using HPLC methods. It was determined that probe 4 was recognized by an antibody, a murine XRI-TF35 mAb, against the 7-dimethylcoumarin-4-acetamide moiety, as micro-equlibrium dialysis (Harvard Apparatus) indicated that XRI-TF35 mAb bound to 4 with a Kd of 1.1±0.2 nM.

Example 10

Evaluation of the Activity of Ammosamides A (IA) and B (IB)

Figure 2:
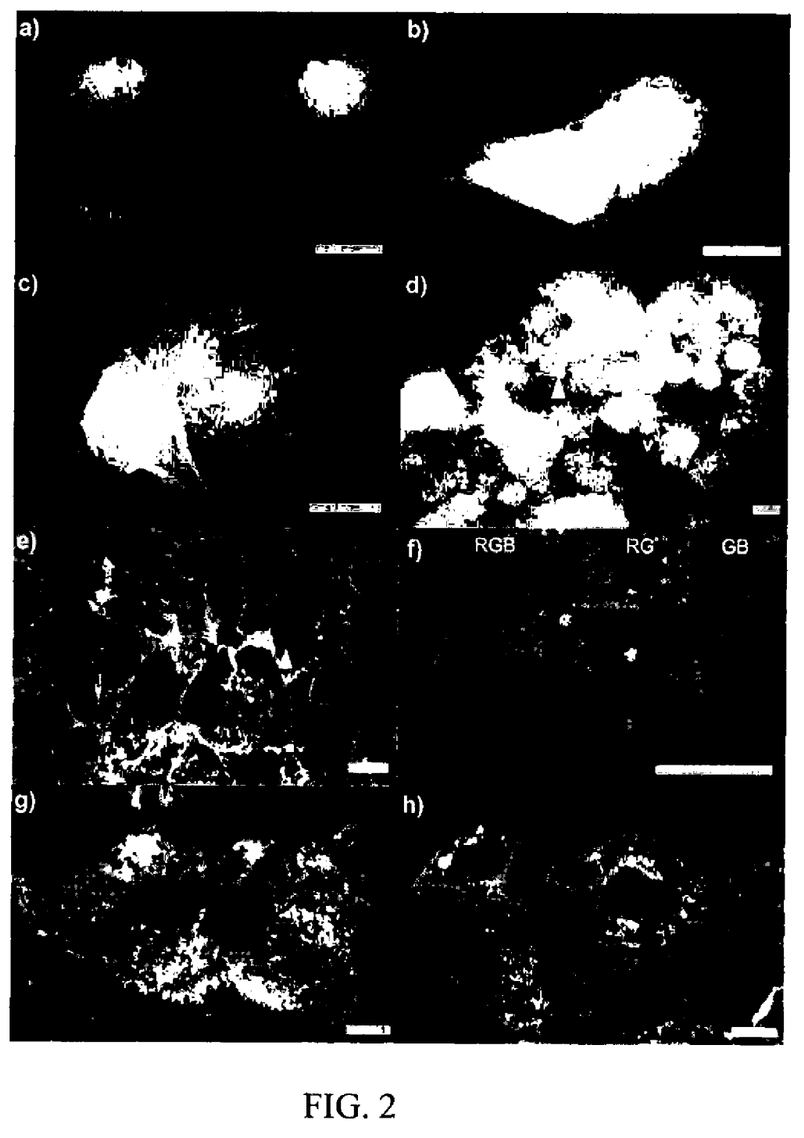
FIG. 2 includes photographs illustrating the images used in the in the evaluation of activity of some compounds of the present invention.

The results of the study of the activity are discussed below with the reference to FIG. 2. Briefly, on FIG. 2, (a-c) are images from 10$^6$ cells incubated with 1 mL of 50 μM probe 5 in DMEM for 15 min. Further on FIG. 2, (a) shows HeLa cells; (b) shows HCT-116 cells; (c) shows PC-3 cells; (d) shows HeLa cells in (a) after incubation at 37° C. with 5% CO$_2$ for 12 hours; (e) is a three-colored confocal microscopy of the cells in (d) after fixation and staining of the nucleus with Syto608 (R), actin with FITC-phalloidin (G) and probe 5 (B). FIG. 2, (f) shows cells in (d) after staining the lysosomes with LysoTracker Red DND-99 (R), actin with FITC-phalloidin (G) and probe 5 (B). Color mixing of R and B channels overlap to form magenta as depicted via three color mixing (RGB). Individual R and B channels are shown by RG and GB composites. FIG. 2, (g-h) shows HCT-116 cells treated for 5 hours with 1 mL of 50 μM in DMEM of probe 5 per 106 cells, fixed and then stained. Microtubules were stained with BODIPY 564/570 paclitaxel (R) and actin with FITC-phalloidin. Colors are denoted as (R)=red, (B)=blue, (G)=green. Bar denotes 10 μm.

Activity of probe 4 (FIG. 1) was compared to that of ammosamide A (1 on FIG. 1). Cytotoxicity data collected with HCT-116 cells indicated that 4 was comparable in activity to IA and IB ($IC_{50}$ values of <1 μM). Florescence microscopy was then used to examine the uptake of probe 4, which was concentrated within HeLa, HCT-116 and PC-3 cells within minutes (FIG. 2). The entire fluorescence from addition of 1 mL of 1 μM in 4 to 106 cells appeared within the cell. Titration studies indicated that the limit of this uptake was 0.24±0.03 pmol/cell, 0.21±0.02 pmol/cell and 0.27±0.04 pmol/cell for HCT-116, HeLa and PC-3 cells, respectively.

Live cell fluorescence microscopy was then conducted to detail the intracellular localization of probe 4. In HeLa cells, probe 4 was observed throughout the cytosol with modest localization apparent within small vesicles observed within the cell (FIG. 2a). Comparable uptake was observed in HCT-116 cells (FIG. 2b). In PC-3 cells, probe 4 appeared less specific appearing throughout the cytosol. After treatment for 15 min, the fluorescence from probe 4 was retained in cells even after repetitive washing with media. Under the same conditions, control 5 (as shown on FIG. 1) was completely washed from all three cell lines. In addition, pretreatment of cells with 1 mL of DMEM containing 10 μM of 1 blocked the uptake of probe 4, thereby further supporting the conclusion that 4 provide a reliable mimetic of 1. Finally, the blue fluorescent stain in FIG. 2a-c remained even after formalin fixation and washing the cells with 95% ethanol suggesting that the uptake of probe 4 was accompanied by either a very strong or covalent interaction.

After 12 hours of incubation, the blue fluorescence from probe 4 was vesiculated (FIG. 2d). This response occurred even after treating the cells with 4 for 15 min followed by washing and incubating them in media free of probe 4. Confocal microscopy of cells co-stained with a panel of organelle markers (FIG. 2e-f) indicated that that the localization occurred in the lysosomes. In particular, the overlap of red fluorescence from the red lysosome stain, LysoTracker Red DND-99, and the blue fluorescence from probe 4 provided strong evidence in support of this observation (FIG. 2f).

Example 11

Evaluation of the Effects of Probe 4 on Cell Cycle

Figure 3:
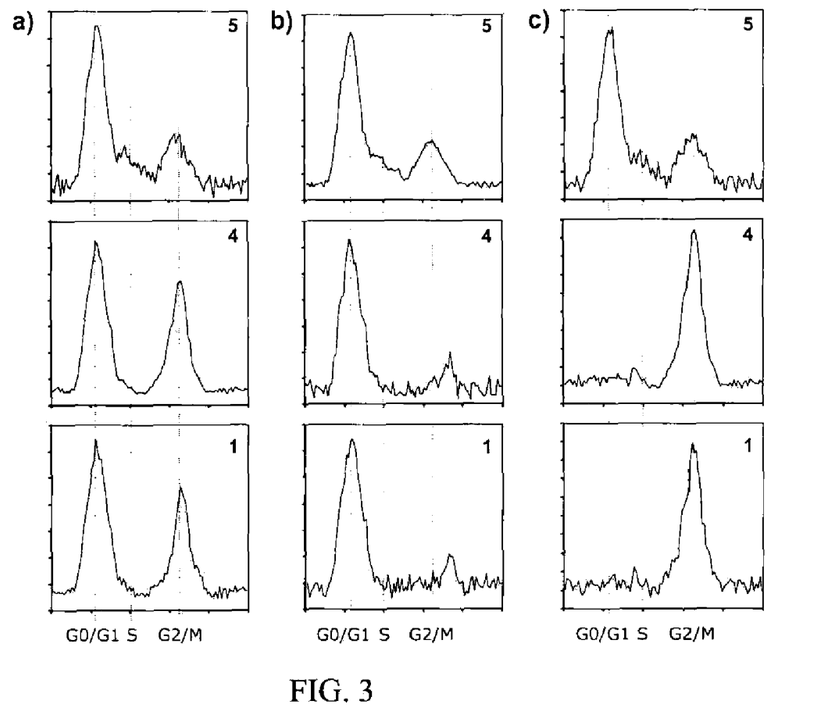
FIG. 3 is a graphic illustration of various cell cycle responses used in the evaluation of activity of some compounds of the present invention.

The results of the study of the activity are discussed below with the reference to FIG. 3. Briefly, FIG. 3 shows cell cycle response for HCT-116 cells treated with either 50 μM of control 5 (as on FIG. 1) (normal cell proliferation), probe 4 or ammosamide A (1) in DMEM per $10^6$ cells. Further, FIG. 3a illustrates cell cycle response for unsyncronized HCT-116 cells, FIG. 3b for HCT-116 cells synchronized and treated at G0 and incubated for 12 hours, and FIG. 3c, for HCT-116 cells synchronized and treated at S and incubated for 12 hours.

The effects of probe 4 on cell cycle were evaluated using FACS analysis. Unsyncronized cells were halted G1, G2 and during mitosis (FIG. 3a). Cells synchronized with L-minosine and treated at G1-phase with probe 4 were halted at the G1/S progression (FIG. 3b). Cells synchronized with thymidine and treated with probe 4 during S-phase were inhibited during G2 and mitosis (FIG. 3c). Comparable cell cycles data were also obtained from studies on ammosamide A (compound 1 on FIG. 1) (FIG. 3a-c), and indicated that probe 4 provided an accurate representation of 1. The complexity of this cell cycle inhibition suggested that identification of the mechanism of action of ammosamide A (1) by evaluating its cellular response would be complex.

Example 12

Screening for Protein Targets

The results of the screening for protein targets are discussed below with the reference to FIG. 4. Briefly, FIG. 4 illustrates co-immunoprecipitation (co-IP) studies. FIG. 4a shows a 3-8% tris-acetate SDS page gel depicting fluorescent bands arising from the co-immunoprecipitation of lysate from 108 HCT-116 cells treated with probe 4 for 12 hours. Co-IP was conducted with Affigel Hz resin containing 12.5 mg/mL of XRI-TF35 mAb. After co-IP, bound protein was eluted from XRI-TF35-Affigel Hz resin with 0.1 M Tris-Cl pH 6.8 (L1), 5 μM of 3 in 0.1 M Tris-Cl pH 6.8 (L2), and 50 μM of 3 in 0.1 M Tris-Cl pH 6.8 (L3). FIG. 4b shows a sample of HCT-116 lysate stained with GelCode blue. FIG. 4c shows GelCode blue staining of the gel in a), and FIG. 4d shows a 4% tris-glycine SDS-page gel depicting fluorescent bands from the co-IP of a 50 μg/ml sample of rabbit skeletal myosin was incubated with 10 μM control 5 in DMEM (L4) or 10 μM probe 4 in DMEM (L5). Upper arrows denote bands of interest.

Using the advantageous dual functionality of the IAF tag, lysates of HCT-116 cells were screened for proteins that bound control 5 (FIG. 1). Co-immunoprecipitation was conducted from lysates of $10^8$ cells treated with 5 μM 5 for 12 hours. The cells were scraped from the plate, concentrated via centrifugation at 300 rpm at 4° C. for 5 min, washed three times with PBS pH 7.2 (5 mL), and lysed in PBS pH 7.2 (0.5 mL) containing protease inhibitor cocktail (Roche) by agitation through a 30 gauge needle.

The crude lysate was centrifuged at 13,000 rpm for 5 min at 4° C. to isolate aggregates to remove insoluble matter and subjected to spin dialysis on a 9 kDa spin filter (iCON, Pierce Biotechnology) to concentrate the lysate to ~1 mg/mL in net protein. Samples of the resulting lysate were precipitated with Affigel Hz containing 12.5 mg/mL of the XRI-TF35 mAb. Protein was then eluted from the resin by treatment with SDS page sample buffer containing 5-50 μM 3 (lanes L2-L3, FIG. 4a).

In five repetitions a band at ~220 kDa appeared after washing the resin with media containing moiety 3 as a vehicle to release bound protein. Western blot analysis with an anti-mouse indicated that this band did contain fragments of the mAb. A sample of this band was submitted to nano-LC/MS/MS analysis indicating strong sequence homology to myosin (22-28% depending on the type and ID myosin chosen).

The immunoprecipitation experiment was repeated using rabbit skeletal muscle myosin. Probe 4 was very effective at labeling this protein with an estimated yield of 35±5% treatment of 100 μg/mL with 10 μM 4 in DMEM for 2 hours at room temperature. The yield of this reaction was based on the relative fluorescent uptake of control 5 after repetitive removal by dialysis on a 9 kDa spin filter (iCON, Pierce Biotechnology). A fluorescent band at ~200 kDa corresponding to the heavy chain of myosin was co-immunoprecipitated from these solutions (L5, FIG. 4b) using methods identical to that used to isolate myosin from HCT-116 cells (FIG. 4a). Control experimentation with control 5 did not return myosin as determined by fluorescent gel analysis (L4, FIG. 4b). This observation confirmed that probe 4 was bound to the heavy chain of myosin type II. The fact that the fluorescence from probe 4 was retained in the myosin band after denatured SDS-page gel analysis suggested that probe 4 (or the dye in probe 4) was covalently attached to myosin. The fact that this observation was only seen with probe 4 and not with dye 3 or control 5, suggested that functionality within the ammosamide core was able to covalently modify myosin.

Given myosins role in cytoskeletal structuring, the effects of probe 4 on actin and microtubule assembly were further studies. HCT-116 cells treated with probe 4 were fibrotic containing greater than a ten-fold increase in F-actin filaments near their plasma membrane (FIG. 2g). This was accompanied by a marked microtubules depolymerization, as apparent by the formation of aggregates throughout the cell (FIG. 2g-h). The combination of these effects could arise from the lack in geometrical assembly of both actin and/or microtubule fragments resulting from the modification of myosin.

Example 13

Histological Studies

The results of histological studies described in this example are discussed below with the reference to FIG. 5. Briefly, FIG. 5 illustrates a microarray containing select *Mus musculus* tissues that was treated for 4 h in 2 mL of 1 µM of probe 4 in PBS pH 7.2. Images from each tissue section were collected using a single exposure time, thereby allowing the intensity to be compared between each image. Control experimentation was conducted in parallel by treating tissue microarray with 1 µM of control 5 in PBS pH 7.2. For all panels, the background from 5 was not visible under the exposure time used for image collection, which include a) adrenal gland, b) bladder, c) bone marrow, d) cerebellum, e) cerebral cortex, f) breast, g) intestine, h) heart, i) kidney, j) lung, k) skeletal muscle, l) pancreas, m) skin, n) spleen, and o) ureter.

Anatomical denominations shown on FIG. 5 are as follows: a=adipose cells, ac=acini, av=alveoli, b r=bronchiole, c=capillaries, cc=chrimaffin cells, cp=crypts, ct=connecting tubules, cx=cortex, d=ducts, d=dermis, e=epithelial cells, ed=epidermis, ei=erythroid island, f=fibroblast cells, gc=granulocytes, iL=islet of Langerhans, lp=lamina propria, m=muscularis, md=medulla, mk=megakaryocyte, my=myocytes, pv=pulminary vetricle, py=pyramidal cells, s=sinusoids, sc=subcutis, sg=sebaceous glands, sr=serosa, tb=trabecular bone, te=transitional epithelium, uc=umbrella cells, and v=villus.

A procedure was used that allowed mouse tissue to be stained with control 5 under conditions in which unbound materials such as control 4 were washed from the tissue. Muscle was a primary target with as indicated by staining in smooth muscle (m in FIGS. 5g and 5o), skeletal muscle (FIG. 5k), cardiac muscle (my in FIG. 5h) and smooth muscle in blood vessels (s in FIG. 5a, e in FIG. 5f, pv in FIG. 5j). However, muscle cells were the only type of cells stained with 5. High concentrations of 5 were found in epithelial cells (te in FIG. 5b), erythroblasts (ei in FIG. 5c), adipocytes (a in FIG. 5f), nerve cells (py in FIGS. 5d-e), dermal cells (d and ed in FIG. 5m), as well as in umbrella cells (uc in FIG. 5d), lamina propria (lp in FIG. 5g), villi (v, FIG. 5g) and intestinal crypts (cp in FIG. 5d), connecting tubules (ct, FIG. 5i), bronchioles (br, FIG. 5j) and islet of Langerhans (iL, FIG. 5l).

Although the invention has been described with reference to the above examples and Attachment 1, the entire contents of which are incorporated herein by reference, it will be understood that modifications and variations are encompassed within the spirit and scope of the invention. Accordingly, the invention is limited only by the following claims.

What is claimed is:

1. An isolated compound having the general structure I:

wherein:

Z is a substituent selected from a group consisting of S and O;

X is a substituent selected from a group consisting of Cl, Br, I;

each of $R_1$ and $R_2$ is a substituent independently selected from a group consisting of H; and each of Y and $Y_1$ is a substituent independently selected from a group consisting of H.

2. The compound of claim 1, wherein each of $R_1$ and $R_2$ is H.

3. The compound of claim 1, wherein Z is S and X is Cl.

4. An isolated compound selected from a group consisting of compounds IA and IB:

5. A compound selected from the group consisting of compounds IC, ID and IE:

6. A pharmaceutical composition, comprising an effective amount of a compound of claim 1 or 4 or 5, and a pharmaceutically acceptable carrier.

7. A method for inhibiting proliferation of mammalian cells, comprising administering to a subject in need thereof a therapeutically effective amount of a compound of claim 1 or 4 or 5 wherein the cells are colon, cervical or prostate cancer cells.

8. The method of claim 7, wherein the proliferation is indicative of colon, cervical or prostate cancer.

9. A method for treating a mammalian cell proliferative disorder, comprising administering to a subject in need thereof a therapeutically effective amount of a compound of claim 1 or 4 or 5, wherein the disorder is cancer of the colon, cervix or prostate.

10. The method of claim 9, wherein the proliferative disorder is colon cancer.

11. A method for producing a compound of claim 1 or 4, comprising:
    a) cultivating a culture of actinomycete strain CNR698-307 or CNR689-291; and
    b) isolating compound I from the culture.

12. The method of claim 11, wherein the compound is selected from a group consisting of compounds IA and IB:

13. An article of manufacture comprising packaging material and a pharmaceutical composition contained within said packaging material, wherein said packaging material comprises a label which indicates that said pharmaceutical composition can be used for treatment of a cell proliferative disorder and wherein said pharmaceutical composition comprises at least one compound of claim 1 or 4 or 5.

14. A method for treating colon, cervical or prostate cancer, comprising administering to a subject in need thereof a therapeutically effective amount of a compound of claim 1 or 4 or 5.

* * * * *